United States Patent [19]
Cuckle et al.

[11] Patent Number: 6,025,149
[45] Date of Patent: Feb. 15, 2000

[54] URINARY SCREENING FOR DOWN SYNDROME AND OTHER ANEUPLOIDIES

[75] Inventors: Howard S. Cuckle, Harrogate; Raymond K. Iles, West Drayton; Timothy Chard, London, all of United Kingdom

[73] Assignee: Yale University, New Haven, Conn.

[21] Appl. No.: 08/675,152

[22] Filed: Jul. 3, 1996

Related U.S. Application Data

[60] Provisional application No. 60/000,945, Jul. 7, 1995.

[51] Int. Cl.[7] .................. G01N 33/53; G01N 33/537; G01N 33/543; G01N 33/48
[52] U.S. Cl. .................. 435/7.94; 435/7.1; 435/7.93; 436/65; 436/501; 436/510
[58] Field of Search .................. 435/7.94, 7.1, 435/7.93; 436/510, 501, 65

[56] References Cited

U.S. PATENT DOCUMENTS

| | | | |
|---|---|---|---|
| 4,874,693 | 10/1989 | Bogart | 435/7 |
| 5,158,895 | 10/1992 | Ashihara et al. | 436/526 |
| 5,240,912 | 8/1993 | Todaro | 514/12 |
| 5,316,953 | 5/1994 | Macri | 436/87 |
| 5,324,667 | 6/1994 | Macri | 436/518 |
| 5,356,817 | 10/1994 | Cole | 436/64 |
| 5,445,968 | 8/1995 | Blithe et al. | 436/510 |

FOREIGN PATENT DOCUMENTS

| | | | |
|---|---|---|---|
| 0421392 | 4/1991 | European Pat. Off. | C12N 5/20 |
| 9002759 | 3/1990 | WIPO | C07K 15/00 |
| 9403804 | 2/1994 | WIPO | G01N 33/49 |

OTHER PUBLICATIONS

Hayashi, et al.: Maternal urinary beta–core fragment . . . : Prenatal Diagnosis: vol. 15: pp. 11–16, Jan. 1995.

Kato, et al.: Beta–Core fragment is a major form of . . . : J. Clin. Endocrin. Metab.: vol. 66, No. 6 : pp. 1197–1201, 1988.

Nicolaides, et al.: Fetal nuchal translucency: ultrasound . . . : Br. Med. J.: vol. 304: pp. 867–869, Apr. 1992.

Kaplan, et al. Clinical Chemistry theory, analysis, and correlation:pp. 691–692 and 1144–1146, 1984.

Canick and Knight, "Multiple–marker Screening for Fetal Down Syndrome," *Contemporary OB/GYN*, pp. 3–12 (Apr. 1992).

Ciba Corning Diagnostics Corp., "Triton® UGP EIA Kit" Brochure (May 1995).

Cole, L.A., "β–Core Fragment (β–Core, UGP or UGF)," *Tumour Marker Update*, 6(3): 69–75 (1994).

Cole et al., "The Deactivation of hCG by Nicking and Dissociation," *Journal of Clinical Endocrinology and Metabolism*, 76(3): 704–710 (1993).

Cole et al., "Urine hCG β–Subunit Core Fragment, a Sensitive Test for Ectopic Pregnancy," *Journal of Clinical Endocrinology and Metabolism*, 78(2): 497–499 (1994).

Cuckle, H., "Screening at 11–14 weeks of gestation: the role of established markers and PAPP–A," *Screening for Down's Syndrome*, Ed. Grudzinskas et al., pp. 311–323 [Cambridge University Press; Cambridge, U.K. (1994)].

(List continued on next page.)

*Primary Examiner*—Ponnathapura Achutamurthy
*Assistant Examiner*—Brett Nelson
*Attorney, Agent, or Firm*—Leona L. Lauder

[57] ABSTRACT

This invention represents a significant advance in prenatal diagnosis by providing urinary screening to detect fetal aneuploidies. Herein disclosed are methods for prenatally assessing risks of a pregnancy being affected by Down syndrome and other aneuploidies by testing maternal urine samples for levels of β-core-hCG. Levels of maternal urinary β-core-hCG above normal indicate a risk that the pregnancy is affected with Down syndrome, and in general risks of other fetal aneuploidies are indicated by either lower than normal or higher than normal maternal urinary β-core-hCG levels. Assessments can be made based on urinary β-core-hCG levels alone or in conjunction with levels of other urinary and/or serum markers, ultrasound parameters and other factors, such as, maternal age.

29 Claims, 1 Drawing Sheet

U.S. PATENT DOCUMENTS

Cuckle et al., "Maternal Urine—A Possibility for use in Screening," *Screening News* (European Down's Syndrome Screening Group Newsletter), 1(2): 5 (Jul. 1994).

Cuckle et al., "Urinary β–Core Human Chorionic Gonadotropin: A New Approach to Down's Syndrome Screening," *Prenatal Diagnosis*, 14: 953–958 (Oct. 1994).

Hayashi and Kozu, "Maternal Urinary β–core Fragment of hCG/Creatinine Ratios and Fetal Chromosomal Abnormalities in the Second Trimester of Pregnancy," *Prenatal Diagnosis*, 15: 11–16 (Jan. 1995).

Kato and Braunstein, "β–Core Fragment Is a Major Form of Immunoreactive Urinary Chorionic Gonadotropin in Human Pregnancy," *J. Clin. Endocrinol. Metab.*, 66: 1197–1201 (1988).

Lee et al., "The purification and development of a radioimmunoassay for β–core fragment of human chorionic gonadotrophin in urine: application as a marker of gynaecological cancer in premenopausal and postmenopausal women," *J. Endocrinol*, 130: 481–489 (1991).

Cole, L. A., "Down syndrome screening using urine β–core fragment test: choice of immunoassay," *Prenatal Diagnosis*, 15: 679–682 (1995) (letter to the editor).

Kellner et al., "Maternal Urine Screening for Fetal Down Syndrome: Comparison of Beta–Core Fragment, Free–Beta Subunit and HCG," *Am. J. Obstet. Gynecol.*, Society of Prenatal Obstetricians (SPO) 1996 Annual Meeting (Hawaii, Feb. 4–10, 1996).

Spencer et al., "Urine Free Beta hCG and Beta Core in pregnancies affected by Trisomy 21," *Am. Soc. Hum. Genet.*, 57: A289 (Oct. 1995) (Abstract).

O'Connor et al., "Recent Advances in the Chemistry and Immunochemistry of Human Chorionic Gonadotropin: Impact on Clinical Measurements," *Endocrine Reviews*, 15(5): 650–683 (1994).

Akar, et al., "A Radioimmunoassay for the Core Fragment of the Human Chorionic Gonadotropin β–Subunit," *Journal of Clinical Endocinology and Metabolism*, 66(3): 538–545 (1988).

O'Connor et al., "Development of Highly Sensitive Immunoassays to Measure Human Chorionic Gonadotropin, Its β–subunit, and β Core Fragment in the Urine: Application to Malignancies," *Cancer Research*, 48: 1361–1366 (Mar. 1, 1988).

Spencer et al., "Free β–hCG as first–trimester marker for fetal trisomy," *The Lancet*, 339: 1480 (Jun. 13, 1992).

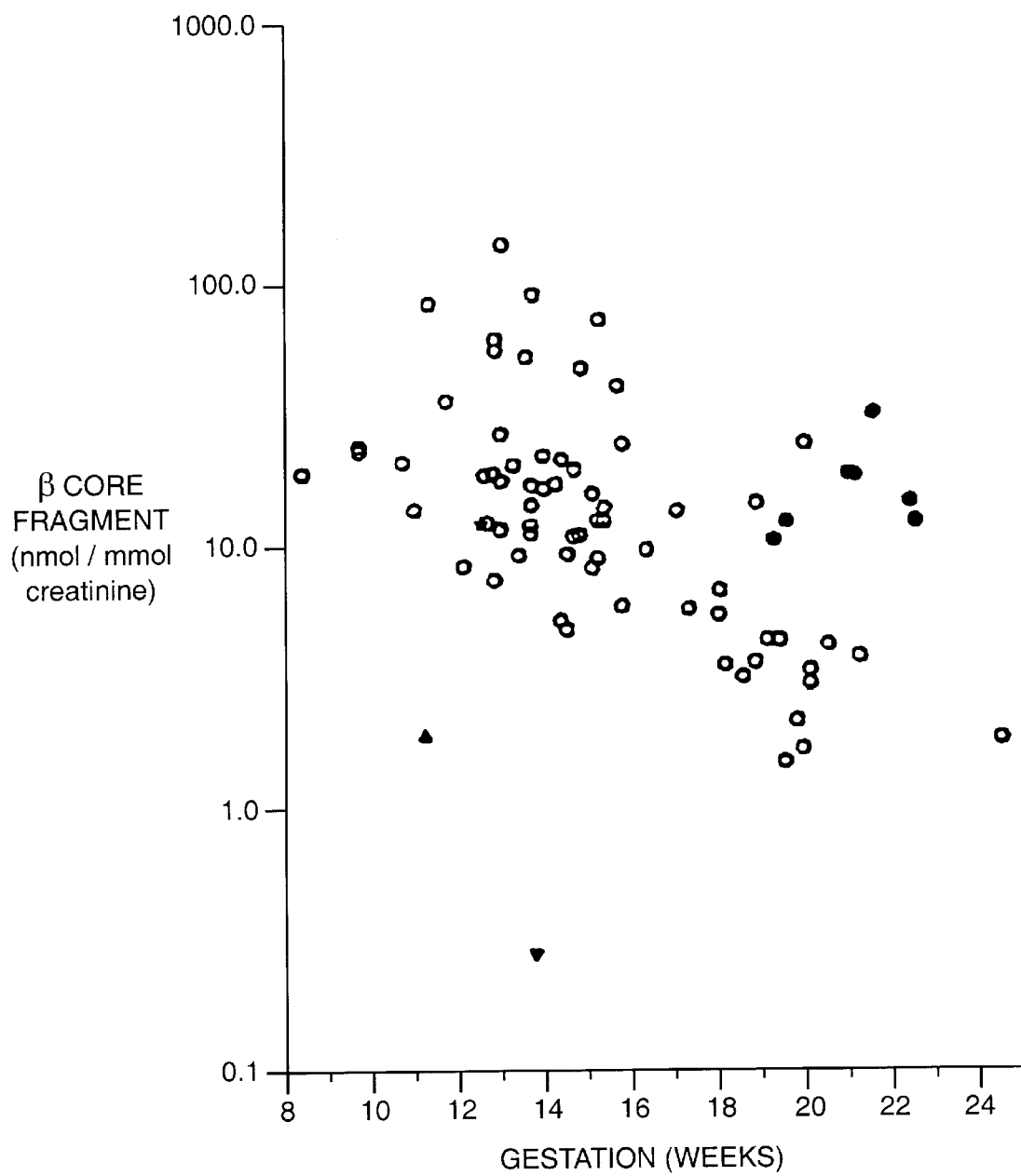
FIG._1

URINARY SCREENING FOR DOWN SYNDROME AND OTHER ANEUPLOIDIES

This application claims the benefit of U.S. Provisional Application Ser. No. 60/000,945 filed Jul. 7, 1995.

FIELD OF THE INVENTION

The present invention is in the field of prenatal diagnosis. It concerns non-invasive methods to screen prenatally for fetal Down syndrome and other fetal aneuploidies by determining the levels of urinary β-core-hCG [also known as urinary gonadotropin peptide (UGP), β-core, β-core fragment, or urinary gonadotropin fragment (UGF)] in maternal urine samples, alone or in conjunction with other markers.

BACKGROUND OF THE INVENTION

Prenatal tests to detect fetal aneuploidies, such as Down syndrome (trisomy 21), Edwards syndrome (trisomy 18), triploidy (69 chromosomes), Klinefelter syndrome (47, XXY), triple X (47,XXX) and Turner syndrome (45,X) among other aneuploidies, by amniocentesis or chorionic villus sampling (CVS) have been available since the late 1960s. Amniocentesis is the most common invasive prenatal diagnostic procedure. In amniocentesis, amniotic fluid is sampled by inserting a hollow needle through the mother's anterior abdominal and uterine walls into the amniotic cavity by piercing the chorion and amnion. It is usually performed in the second trimester of pregnancy. CVS is performed primarily during the first trimester, and involves collecting cells from the chorion which develops into the placenta.

Another invasive prenatal diagnostic technique is cordocentesis or percutaneous umbilical cord blood sampling, commonly known as fetal blood sampling. Fetal blood sampling involves obtaining fetal blood cells from vessels of the umbilical cord, and is often performed about the 20th gestational week.

Amniocentesis is used selectively because it presents a risk of about 1% of inducing spontaneous abortion. CVS and fetal blood sampling carry a similar or higher risk of inducing abortion, and there is also concern that those procedures may lead to fetal limb malformations in some cases. Thus, amniocentesis, CVS and fetal blood sampling are procedures that are only employed if a pregnancy is considered at high risk for a serious congenital anomaly. Thus, some means is required to select those pregnancies that are at a significant risk of an aneuploidy, such as, Down syndrome, to justify the risks of such invasive prenatal diagnostic procedures, as amniocentesis, CVS and fetal blood sampling.

Prior to 1983, the principal method for selecting pregnancies that had an increased risk for genetic defects was based on maternal age, that is, the older the age of the mother, the higher the risk that the pregnancy would be affected by aneuploidy. In 1974, biochemical screening for neural tube defects by measuring alpha-fetoprotein (AFP) began. In 1984, the use of the AFP screen was additionally adopted for the detection of Down syndrome. Since the early 1990s, a multiple marker blood test has been used to screen for that disorder. A common version of that test is the three marker triple test. The triple screen measures AFP, human chorionic gonadotropin (hCG) and unconjugated estriol ($uE_3$) in the serum of pregnant women.

The triple screen provides a means to screen the population of pregnant women to determine which pregnancies are at risk for Down syndrome and other serious genetic defects. The risk is calculated based on the results of the screen, along with other cofactors, such as, maternal age, to determine if the risk is high enough to warrant an invasive diagnostic procedure, such as, amniocentesis, CVS or fetal blood sampling. Such prenatal screens, as the triple screen, can be used either to reduce the need for amniocentesis or to increase genetic defect detection for the same amount of amniocentesis. "The efficiency of the Triple test is projected to be one case of fetal Down syndrome detected for every 50 amniocenteses performed." [Canick and Knight, "Multiple-marker Screening for Fetal Down Syndrome," *Contemporary OB/GYN*, pp. 3–12 (April 1992).]

Although pregnant women who are 35 years or older are the standard high risk group for fetal Down syndrome affected pregnancies, screening also needs to be applied to young women because although they are at lower risk, most affected pregnancies are in young women. Approximately 80% of babies born with Down syndrome are born to mothers under 35. ["Down Syndrome Screening Suggested for Pregnant Women under 35," *ACOG Newsletter*, 38(8): 141 (Aug. 1994).]

The triple screen combines the analysis of three markers from serum to reduce false positive results (which result in the performance of unnecessary invasive procedures) and false negatives (in which serious genetic defects, such as, trisomy 21, go undetected). In women under 35, the double screen (AFP and hCG) can pick up about half of Down syndrome cases and a large proportion of other chromosome defects during the second trimester. The triple screen (AFP, hCG and $uE_3$) increases the detection rate by 5–10% of Down syndrome and a further increase in the detection of all other serious chromosome defects, thus decreasing the number of false-positives. However, such rates mean that the double and triple screens still fail to detect a significant number of Down syndrome and other aneuploidy affected pregnancies.

Although the triple screen has a suggested screening period of 15 to 20 weeks gestation, such screening has been recommended between weeks 16–18 to maximize the window for spinal bifida detection. [Canick and Knight, supra (April 1992).] A 1992 survey of prenatal maternal serum screening for AFP alone or for multiple analyses reported that very few such screenings occurred in the thirteenth or earlier week of gestation. [Palomaki et al., "Maternal Serum Screening for Fetal Down Syndrome in the United States: A 1992 Survey," *Am. J. Obstet. Gynecol.*, 169(6): 1558–1562 (1992).] The triple screen thus suffers from the additional problem that once a risk of a genetic defect is predicted, and amniocentesis or another invasive prenatal definitive diagnostic procedure is performed to diagnose the genetic defect, such as Down syndrome, it is at an advanced date of gestation, when termination of a pregnancy can be more physically and emotionally trying for the mother, and when certain less traumatic abortion procedures, such as, vacuum curettage, may not be available.

The limitations of the triple screen and the adverse consequences of unnecessary, potentially harmful and expensive invasive prenatal diagnostic procedures, such as, amniocentesis, have led to a search for more discriminatory markers for prenatal screening of Down syndrome and other aneuploidies. Of the maternal serum markers in routine use, human chorionic gonadotropin (hCG) is by far the most discriminatory. HCG is a glycopeptide hormone produced by the syncytiotrophoblasts of the fetal placenta, and has a molecular weight of about 38 kilodaltons (kd). It can be detected by immunoassay in the maternal urine within days after fertilization and thus provides the basis of the most commonly used pregnancy tests.

The intact hCG molecule is a dimer comprising a specific β subunit (145 amino acids) non-covalently bound to an α subunit (92 amino acids), which is common to other glycoproteins. Maternal serum levels of both intact hCG and the free β-subunit are elevated on average in Down syndrome but the extent of elevation is greater for free β-hCG [Spencer, K., *Clin. Chem.*, 37: 809–814 (1991); Spencer et al., *Ann. Clin. Biochem.*, 29: 506–518 (1992); Wald et al., *Br. J. Obstet. Gynaecol.*, 100: 550–557 (1993)]. HCG is detected in the serum and urine of pregnant women, as are the free α- and β-subunits of hCG, and degradation products of hCG and of free β-subunit hCG.

The terminal degradation product of the β-subunit of hCG is called β-core-hCG, or alternatively β-core fragment, β-core, urinary gonadotropin peptide (UGP), or urinary gonadotropin fragment (UGF). β-core-hCG is excreted into urine [Nislua et al., *J. Steroid. Biochem.*, 33: 733–737 (1989); Cole et al., *J. Clin. Endocrinol. & Metab.*, 76: 704–710 (1993)].

β-core-hCG has been found in the urine of pregnant women carrying normal fetuses, and also in the urine of patients with gestational trophoblastic and non-trophoblastic malignancies [Cole et al., "Urinary Human Chorionic Gonadotropin Free B-subunit and B-core Fragment: A New Marker of Gynecological Cancers," *Cancer Res.*, 48: 1356–1360 (1988); Cole et al., "Urinary Gonadotropin Fragments (UGF) in Cancers of the Female Reproductive System," *Gynecol. Oncol.*, 31: 82–90 (1988); O'Connor et al., "Development of Highly Sensitive Immunoassays to Measure Human Chorionic Gonadotropin, Its β-subunit, and β-core Fragment in the Urine: Application to Malignancies," *Cancer Res.*, 48: 1361–1366 (1988); and Akar et al, "A Radioimmunoassay for the Core Fragment of the Human Chorionic Gonadotropin β-subunit," *J. Clin. Endocrinol. and Metab.*, 66: 538–545 (1988).] β-core-hCG has also been found to be associated with certain ovarian cancers. [Cole and Nam, "Urinary Gonadotropin Fragment (UGF) Measurements in the Diagnosis and Management of Ovarian Cancer," *Yale J. Bio. and Med.*, 62: 367–378 (1989).]

The invention disclosed herein concerns the finding that β-core-hCG levels in urine samples taken from pregnant women can be used for prenatal screening to detect fetal aneuploidies. β-core-hCG levels in such maternal urine samples were found on average to be elevated above normal in pregnancies affected by fetal Down syndrome, Turner syndrome, Klinefelter syndrome and triple-X, most notably in Down syndrome cases, and to be reduced in the presence of other serious aneuploidies such as, Edwards syndrome and triploidy. The observed median level in Down syndrome affected pregnancies in the second trimester (6.11 MOM: 95% confidence interval 3.7 to 10.0) has been found to be over three times greater than the corresponding median level for intact hCG in maternal serum (2.0 MOM; 1.9–2.1) and free β-hCG (2.3 MOM; 2.1–2.5).

Further, the urinary screening methods of this invention provide higher detection rates of aneuploidies than the maternal serum screening methods. For example, as shown herein (Example 2), testing for β-core-hCG levels in the second trimester alone generates a detection rate of fetal Down syndrome of about 80% at a 5% false-positive rate. Further development of the methods of this invention is expected to increase that detection rate. In comparison, teting for maternal serum hCG or free β-hCG alone generates no more than a 45% detection rate at a 5% false-positive rate [Wald et al., *Br. Med. J.*, 297: 883 (1988); Spencer, K., *Clin. Chem.*, 37: 809 (1991)]. The present standard methods of maternal serum screening with multiple biochemical markers, which include various combinations of AFP, hCG, free β-hCG, free α-hCG and $uE_3$ used in conjunction with maternal age can optimally detect 72% of Down syndrome cases at a 5% false-positive rate [Wald et al., *Prenat. Diagn.* 14: 707 (1994)].

This invention in providing a means of prenatal screening using urinalysis instead of serum testing has important advantages. Urine tests are less expensive than serum testing, avoid the safety issues and handling risks associated with the collection and storage of blood samples, as well as the invasiveness and discomfort of phlebotomy. Urine samples can be easily collected and shipped, if necessary, where women have limited access to medical testing facilities because of geography or socio-economic status. β-core-hCG is stable to changes in temperature, pH, and storage time at −20 and 40° C. Thus, the methods of this invention provide for more discriminatory, cheaper, less invasive and more geographically accessible means for prenatal screening for fetal aneuploidies, than had been provided by former methods of screening based on maternal serum markers.

Further, the maternal urine screening methods of the instant invention can be used not only in the second trimester as maternal serum screening methods are predominantly used, but also in the first trimester. As indicated above, there are disadvantages to second trimester testing, in that delays in confirming a fetal aneuploidy diagnosis result in more traumatic abortion procedures being necessitated. Also, the emotional attachment and expectations of the pregnant woman and her family for a healthy baby, grow during the pregnancy, making the abortion decision more difficult later in the gestational term. The instant invention provides the benefits of urinalysis and may also avoid the problems of second trimester prenatal screening. Thus, the instant invention represents a significant advance in the field of prenatal diagnosis.

SUMMARY OF INVENTION

The instant invention provides improved methods of prenatal screening for fetal aneuploidies by detecting and quantitating β-core-hCG in maternal urine samples and comparing the levels to those found in maternal urine samples from normal pregnancies at the same gestational age. The methods for determining β-core-hCG levels in maternal urine samples can comprise antibody and non-antibody methods, but preferably comprise the use of immunoassays.

The examples herein show that urinary β-core-hCG levels are elevated on average in. pregnancies affected by fetal Down syndrome and may be reduced or elevated in the presence of other less common but serious aneuploidies. In Example 1, the observed median level in Down syndrome (6.11 MOM; 95% confidence interval 3.7–10.0) is considerably greater than the corresponding median level for maternal serum intact hCG (2.0 MOM; 1.9–2.1) and free β-hCG (2.3 MOM; 2.1–2.5) derived from all published studies combined [Cuckle and Lilford, *Br. Med. J.*, 305: 1017 (1992)]. The findings thus indicate that urinalysis is a candidate as a routine screening modality for prenatal screening for aneuploidy.

Representative fetal aneuploidies for which the methods of the instant invention screen include Down syndrome, Edwards syndrome, triploidy, Klinefelter syndrome, Turner syndrome, and triple-X. On average, β-core-hCG levels are elevated above normal in maternal urine samples from pregnancies affected by Down syndrome, Turner syndrome, Klinefelter syndrome and triple-X, and β-core-hCG levels are lower than normal in maternal urine samples from pregnancies affected by Edwards syndrome and triploidy.

Maternal urine samples are preferably tested according to the methods of this invention in the first or second trimesters. The risk assessment of fetal aneuploidy may be based upon the β-core-hCG level in a maternal urine sample alone or in conjunction with the level of one or more other urinary markers in said urine sample and/or in conjunction with the level of one or more serum markers in a serum sample from the woman carrying the pregnancy under analysis, wherein an abnormal level of any of the urinary or of any of the serum markers indicates an increased risk of fetal aneuploidy. Further, the risk assessment may be made based upon the level of β-core-hCG in said urine sample in conjunction with other factors, as for example, maternal age wherein the older the maternal age, the greater the risk of fetal aneuploidy. A further example of other factors that can be used in conjunction with UGP levels in maternal urine samples to assess the risk of pregnancies being affected by fetal aneuploidies are ultrasound markers, wherein an abnormal ultrasound marker indicates an increased risk of fetal aneuploidy.

BRIEF DESCRIPTION OF THE FIGURE

FIG. 1 shows β-core-hCG concentration according to gestational age in seven singleton pregnancies with Down syndrome (blackened circles), one with Edwards syndrome (blackened triangle), one with triploidy (inverted blackened triangle), one twin discordant for Down syndrome (star), and 67 controls (open circles).

DETAILED DESCRIPTION

The following abbreviations are used herein:

Abbreviations

16α-OH-DHAS—16α-hydroxydehydroepiandrosterone sulphate
α-hCG—α-subunit of human chorionic gonadotropin
AFP—alpha-fetoprotein
AMN—amniocentesis
BL—bioluminescent
CCD—Ciba Corning Diagnostics Corporation
CL—chemiluminescent
CvS—chorionic villus sampling
EIA—enzyme immunoassay
fmol—femtomole
GA—gestational age
hCG—human chorionic gonadotropin
HRP—horseradish peroxidase
kd—kilodaltons
L—liter
LNMP—last normal menstrual period
MBP—major basic protein
mg—milligram
ml—milliliter
mmol—millimole
MOM—multiples of normal gestation-specific median
ng—nanogram
nmol—nanomole
NMR—nuclear magnetic resonance
PAPP-A—pregnancy-associated plasma protein A
pmol—picomole
PMP—paramagnetic particle
proMBP—proform of eosinophilic major basic protein
SD—standard deviation
tE—total estrogen
TMB—tetramethyl benzidine TOP—termination of pregnancy
$uE_3$—unconjugated estriol
UGF—urinary gonadotropin fragment
UGP—urinary gonadotropin peptide

Definitions

Alternative terms used in the art for β-core-hCG include urinary gonadotropin peptide (UGP), β-core fragment, β-core, and urinary gonadotropin fragment (UGF).

The first trimester is herein defined as 14 completed weeks (14 weeks, 6 days) from the onset of a pregnant woman's last normal menstrual period (LNMP).

Intact hCG is a term that defines hCG in its dimeric form when its α and β subunits are non-covalently bound together.

Total hCG is a term that includes intact hCG and either its free α subunit or its free β subunit.

"Aneuploidy" is herein defined to refer to any deviation from the human diploid number of 46 chromosomes.

The term "antibodies" is defined herein to include not only whole antibodies (monoclonal and polyclonal) but also biologically active fragments of antibodies, preferably fragments containing the antigen binding regions.

Representative Embodiments

Herein are disclosed methods for prenatally assessing risks of a pregnancy being affected by fetal aneuploidy, such as, Down syndrome, comprising testing maternal urine samples for differences in the levels of β-core-hCG from normal levels. For example, a β-core-hCG level elevated above normal would indicate a risk of a pregnancy being affected by Down syndrome, Turner syndrome, Klinefelter syndrome, or triple-X, among other aneuploidies, whereas a level below normal would indicate a risk of the pregnancy being affected by a fetal aneuploidy, such as, Edwards syndrome or triploidy among other aneuploidies.

β-core-hCG is a glycopeptide with a molecular weight of about 10 kilodaltons (kd) [Birken et al., *Endocrinol.*, 123: 572–573 (1988)]. β-core-hCG has an amino acid sequence related to the β-subunit of hCG. β-core-hCG is comprised of β-subunit residues 6 through 40 attached by disulfide linkages to residues 55 through 92. β-core-hCG is glycosylated but lacks the sialic- acid and O-linked carbohydrate residues present on the hCG β subunit. [Birken et al., supra.]

Unlike hCG which is conventionally measured in maternal sera, β-core-hCG is measured in maternal urine samples according to this invention. Corrections are made for creatinine excretion to control for dilution variability in the urine samples. Levels of β-core-hCG are expressed as multiples of the normal gestation-specific median (MOM).

One preferred embodiment of the prenatal screening methods of this invention is expressed as follows.

A method for prenatally determining whether there is a significant risk of a pregnancy being affected by fetal aneuploidy comprising:

(a) taking a maternal urine sample;
(b) testing said maternal urine sample to determine the level of β-core-hCG in said sample;
(c) determining whether the level of β-core-hCG in said sample is above or below a level of β-core-hCG that is normal in urine samples from women whose pregnancies are unaffected by aneuploidy, and whose pregnancies are at about the same gestational age as the pregnancy under analysis; and (d) determining whether there is a significant risk of fetal aneuploidy based upon the level of β-core-hCG in said sample, wherein a level above or below said normal level indicates that there is a significant risk of fetal aneuploidy.

The β-core-hCG levels determined by the methods of this invention can be used to assess fetal aneuploidy risk either alone or in conjunction with results from other screening tests with other serum markers, urinary markers, ultrasound markers, and/or other factors, such as, maternal age, maternal health, and maternal weight. For example, maternal age and β-core-hCG levels are independent predictors of Down syndrome risk, as is true for each of the commonly used serum markers. Therefore, after performing the prenatal screening methods of this invention, the risk of a Down syndrome affected pregnancy can be calculated by multiplying the age-related risk by a likelihood ratio derived from the β-core-hCG level found in the maternal urine sample in relation to control samples.

Other urinary markers which could be preferred for assessing the risk of a Down syndrome affected pregnancy in conjunction with β-core-hCG levels, include pregnancy-associated plasma protein A (PAPP-A), dimeric inhibin, total estrogen (tE), unconjugated estriol ($uE_3$), total estriol ($tE_3$), AFP and proform of eosinophilic major basic protein (proMBP), among other urinary marker possibilities.

In general, a positive result from the screening methods of this invention is an indicator that a more invasive prenatal diagnostic procedure, such as, amniocentesis, CVS or fetal blood sampling, should be performed to determine definitively whether the pregnancy is affected with a fetal aneuploidy, such as Down syndrome.

Gestation-specific medians for β-core-hCG can be calculated by weighted non-linear regression from the values for control urine samples. To account for variations in the concentrations of urine samples, β-core-hCG levels can be expressed in terms of creatinine. Gestational ages of cases and controls can be determined by ultrasound parameters and/or by last menstrual period dating.

The control samples are preferably taken from a population of pregnant women that are matched as well as practicable to the population from which the pregnant woman who provided the test sample comes. For example, population parameters could include race, ethnicity, and geographical location, among other parameters.

The prenatal screening methods of this invention are preferably used to test first and second trimester maternal urine samples. The benefits of such earlier screening results are discussed above in the Background.

The reason for the elevation of both intact hCG and its fragments in maternal serum and urine from pregnancies affected with Down syndrome is not known. The instant inventors observed a greater elevation in urinary β-core-hCG than that seen for intact, total and free β-hCG in maternal serum. Although those observations support the idea that there is molecular instability in affected pregnancies [Rotmensch et al., *Am. J. Obstet. Gynecol.*, 166: 354 (1992)], there may very well be other explanations and further research, e.g. with a large series of paired blood and urine samples, may illuminate the underlying mechanisms.

Many methods can be used to detect and quantitate β-core-hCG in maternal urine samples. Antibody and non-antibody methods can be used. A variety of immunoassay formats can be used as set forth below. Non-antibody methods include, for example, chromatographic procedures that separate β-core-hCG from other components of urine, such as, high pressure liquid chromatography (HPLC) and mass spectrometry, alone or in combination; fluorometric detection means; nuclear magnetic resonance (NMR); and the use of non-antibody receptors and other binding proteins that may exist cellularly or in serum.

The embodiments outlined herein are representative of a wide number of assay methods that can be used in accordance with this invention. There are many variations and modifications of such outlined embodiments within the skill of one in the art.

Urine Concentration

The prenatal screening methods of this invention do not require uniformity in the volume of urine obtained from each pregnant woman of the control or case groups or the time of voiding. Although 24-hour maternal urine specimens can be used in the methods of this invention, for simplicity, economy and universality, the methods of this invention preferably employ random maternal urine samples, rather than 24-hour specimens. However, when random urines are used, the sample concentration requires correction.

A standard approach can be used of measuring creatinine levels and dividing each marker value by that level. For example, the β-core-hCG concentration can be corrected for creatinine and expressed for example, in nmol/mmol creatinine.

Creatinine content in urine can be measured by the Jaffe method using a Monarch 200 centrifugal analyzer as described in Example 1. Creatinine levels can also be measured on a Synchron CX-5 chemistry analyzer (Beckman Instruments; Brea, Calif., USA) or by other methods known in the art.

Standardizing the time of voiding (e.g. early morning) may be helpful to decrease the concentration variability. Other concentration measures, such as, specific gravity, optical density or osmolarity, may also be useful. Dividing a marker level by a non-proportional statistical method may also be preferred over dividing a marker level by the concentration.

Other Covariables

Preferably, the screening methods of this invention include the comparison of results to normals and in making risk assessments include covariables. Several factors have been found which alter maternal serum hCG levels including maternal smoking (e.g, cotinine levels) maternal weight and the presence of twins. Adjustment for those covariables reduces the spread of values and so increases the aneuploidy detection rate.

Other Markers

"Population screening is the identification, among apparently healthy individuals, of those who are sufficiently at risk of a specific disorder to justify a subsequent diagnostic test or procedure. This implies the testing of all pregnancies in order to identify those few at a great enough risk to warrant an invasive diagnostic procedure, such as amniocentesis." [Canick et al., "Maternal Serum Screening for Aneuploidy and Open Fetal Defects," *Prenatal Diagnosis*, 20(3): 443 (September 1993).] A higher than normal or lower than normal result from a screening method according to this invention indicates a higher risk of fetal aneuploidy, whereas a normal result does not necessarily mean that a fetus is free of aneuploidy but that the fetus is at a lower risk of a genetic defect.

Screening detection rates can be increased and false positives can be decreased by combining the results of a prenatal screening method with results of screening with other markers and assessing the results in conjunction with other factors. When considering the cost of a second or third marker, it has to be weighed against the extra costs incurred without their use in additional amniocentesis tests for the affected pregnancies. [Cuckle, H. S., Clin. Chem., 38(9): 1687–1689 (1992).]

The results from the prenatal screening methods of this invention can be used alone or in conjunction with results from other screening tests with other serum markers, urinary markers, ultrasound markers, and/or other factors, such as, maternal age, maternal health, and maternal weight, to assess the risks of a pregnancy being affected by aneuploidy, such as, Down syndrome. Various serum markers and urinary markers could be combined to enhance the detection rate of fetal aneuploidies. The serum sample can be tested for free β-hCG, AFP, and $uE_3$ and/or intact hCG or α-hCG among other markers, for example by using an RIA [e.g., Kodak Clinical Diagnostics Ltd; Rochester, N.Y. (USA)] or time-resolved fluorometric assay [Wallac Oy]. Prenatal screening could comprise testing paired blood and urine samples from each mother. For example, markers such as alpha-fetoprotein (AFP) and unconjugated estriol ($uE_3$) might be tested in the blood sample and β-core-hCG in the urine sample.

β-core-hCG measurements can be combined with other markers in serum and/or in urine as exemplified by PAPP-A and related chemicals, such as, major basic protein (MBP) and proMBP; intact hCG, free α-hCG, free β-hCG and other hCG species; AFP; $uE_3$ and precursors/breakdown products; maternal estrogen and precursors/breakdown products, such as, 16α-OH-DHAS; and all species of inhibin.

As indicated in Example 2, infra, other urinary markers, notably tE, may be used in conjunction with β-core-hCG to enhance the detection rate of Down syndrome. The tE level reduction in urine in Down syndrome (Example 2) was similar to that found for $uE_3$ in maternal serum. Example 2 shows that an expected detection rate for β-core-hCG and tE is high—an estimated 82% detection rate for 5% false-positive rate. Such a detection rate is greater than the 67% rate predicted for maternal serum screening with hCG, $uE_3$ and AFP [Wald et al., Br. J. Obstet. Gynaecol., 99: 144 (1992)] or the 59% rate with free β-hCG and AFP [Spencer et al., Ann. Clin. Biochem., 29: 506 (1992)]. That result indicates that urinalysis may be able to replace serum screening. Both established and newer serum markers are candidate maternal urinary markers.

Preferred urinary markers for assessing the risks of a Down syndrome affected pregnancy in conjunction with β-core-hCG include PAPP-A, dimeric inhibin, tE, $uE_3$, $tE_3$, AFP and proMBP, among other urinary marker possibilities. Particularly preferred potential urinary markers to be used in conjunction with β-core-hCG to assess fetal Down syndrome risks are PAPP-A, dimeric inhibin, 16α-OH-DHAS and tE.

PAPP-A may be found in first trimester urine samples, at levels significantly reduced below normal in Down syndrome affected pregnancies. An assay for dimeric inhibin is described in Cuckle et al., "Maternal Serum Inhibin Levels in Second-Trimester Down's Syndrome Pregnancies," Prenatal Diagnosis, 14: 387–390 (1994). That assay could be adapted for urine testing. Dimeric inhibin may be useful in the first trimester.

Total estrogen can be measured by a continuous flow system based on the Kober reaction [Lever et al., "Improved estriol determination in a continuous flow system," Biochem. Med., 8: 188–198 (1973)]. Total estrogen could be measured as μmol/mmol creatinine.

By the second trimester, maternal estrogen is largely derived from fetal hepatic and placental metabolism of precursors secreted by the fetal adrenal glands [Oakey, R. E., Vitamins and Hormones, 28: 1 (1970)]. Thus, measurement of estrogen production reflects fetal and placental function. The unconjugated estrogens formed by the placenta are rapidly converted to conjugated forms by addition of glucuronic and sulphuric acid residues, before excretion. The inventors measured those urinary conjugated estrogens, mostly estriol conjugates. By contrast, in maternal serum screening for Down syndrome, unconjugated estriol is measured rather than the more abundant conjugated forms.

Both approaches appear to provide similar information. The rate of increase in urinary tE per week of gestation among the controls in Example 2 (24%) was similar to the weekly increase in maternal serum $uE_3$ at the same time in pregnancy. Also the median urinary tE level in the 24 Down syndrome pregnancies (0.74 MOM) tested in Example 2 was close to the median maternal serum $uE_3$ level (0.73 MOM) in a total of 363 affected pregnancies from published series. [Cuckle, H. S., IN: Screening for Down's Syndrome, pp. 311–323 (Grudzinskas et al. eds.; Cambridge University Press; Cambridge U.K.; 1994).] Moreover, others have demonstrated a close correlation (R=0.77) between urinary total estrogen excretion and plasma unconjugated estriol concentration in late pregnancy [Allen and Lachelin, Br. J. Obstet. Gynaecol., 85: 278 (1978)].

The method used in Example 2 herein assesses excretion of a combination of 16α-hydroxyestrogens (e.g. estriol) and deoxyestrogens (e.g. estrone, estradiol). Whether application of a different method targeted at one particular estrogen (e.g., estriol-16α-glucosiduronate) offers the same detection rate awaits investigation.

Improved discrimination may be achieved by measuring precursors directly in the urine. A preferred precursor is 16α-hydroxydehydroepiandrosterone sulphate (16α-OH-DHAS). Through a placental process known as aromatization, this compound is the precursor of more than 85% of estrogens in late pregnancy urine. 16α-OH-DHAS has a relatively low affinity for the series of placental enzymes which catalyze its conversion to estriol [Purohit and oakey, J. Ster. Biochem., 33: 439–448 (1989)]. Any decline in placental function in Down syndrome might well exaggerate the quantity which escapes aromatization. In the extreme condition of steroid sulphatase deficiency, for example, sufficient 16α-OH-DHAS avoids aromatization and is excreted in maternal urine to provide a secure diagnostic test for the condition [Wilmot et al., Ann. Clin. Biochem., 25: 155–161 (1988)].

Also, physical measurements, such as ultrasound markers can be used in combination with urinary β-core-hCG levels to assess prenatally the risk of fetal aneuploidy. Exemplary ultrasound markers include nuchal translucency [Nicolaides et al., Br. Med. J., 304: 867 (1992)], femur length, humerus, cephalic index, ventricular size, and ultrasound detected defects in the heart, gut, and organs, among other physical markers.

Immunoassays

The prenatal screening methods of this invention can be in any standard immunoassay format, such as, sandwich assays, competition assays, bridge immunoassays, among other formats well known to those of skill in the art. [See, for example, U.S. Pat. Nos. 5,296,347; 4,233,402; 4,034,074;

and 4,098,876.] For example, a competitive radioimmunoassay (RIA), a sandwich EIA or sandwich RIA may be preferred immunoassay formats. A sandwich assay is a preferred format of this invention, and a sandwich RIA or EIA is a further preferred format.

A particularly preferred immunoassay to detect and quantitate β-core-hCG is described in Examples 1 and 2, infra wherein a modification of a radioimmunoassay method described in Lee et al., *J. Endocrinol.*, 130: 481–489 (1991) is used. Another particularly preferred immunoassay method of this invention would employ the Triton® UGP EIA Kit from Ciba Corning Diagnostics Corp. (Alameda, Calif.; USA).

Although the assay used in Examples 1 and 2 [modified from Lee et al., *J. Endocrinol.*, 130: 481–489 (1991)] cross-reacts with purified preparations of intact hCG and free β-hCG, it is considered unlikely that the differences in β-core-hCG levels that were found in affected and unaffected pregnancies are due to interference with other markers. Based on published data on urinary measurements at 4–6 weeks' gestation of all three forms of hCG corrected for creatinine [Cole et al., *J. Clin. Endocrinol. Metab.*, 78: 497–499 (1994)], it was calculated that the β-core fragment has twice the molar concentration of the intact molecule and 200 times that of the free β-subunit. As pregnancy progresses, the molar excess of urinary β-core-hCG increases further [Kato and Braunstein, *J. Clin. Endocrinol. Metab.*, 66: 1197–1201 (1988)]. Thus, the 6.9% and 18% cross-reaction for intact hCG and free β-hCG, respectively, represents a small contamination in the assay used.

Variations of the representative embodiments of the methods of this invention within conventional knowledge of those of skill in the art are considered to be within the scope of the instant invention. Preferred variations and more detailed embodiments are identified in the following sections.

Reference is made hereby to standard textbooks of immunology that contain methods for carrying out various immunoassay formats that can be adapted from those specifically represented herein. See, for example, *Molecular Bioloav and Biotechnology: A Comprehensive Desk Reference* (Ed. R. A. Meyers) [VCH Publishers, Inc., New York, N.Y. (1995)]; Moore and Persaud, *The Developing Human: Clinically Oriented Embrvology*, 5th Edition [W. B. Saunders Company; Philadelphia/London/Toronto/Montreal/Sydney/Tokyo (1993)]; Darnell et al., *Molecular Cell Biology*, W. H. Freeman and Company (N.Y. 1990); Colowick et al., *Methods in Enzymology*, Volume 152 [Academic Press, Inc. (London) Ltd. (1987)]; and Goding J. W., *Monoclonal Antibodies: Principles and Practice: Production and Application of Monoclonal Antibodies in Cell Biology, Biochemistry, and Immunology* [Academic Press Inc. (London) Ltd.; 1983.]

Antibodies

As indicated above, the term "antibodies" is defined to include not only whole antibodies but also biologically active fragments of antibodies, preferably fragments containing the antigen binding regions. Such antibodies may be prepared by conventional methodology and/or by genetic engineering.

Antibody fragments may be genetically engineered, preferably from the variable regions of the light and/or heavy chains (VH and VL), including the hypervariable regions, and still more preferably from both the VH and VL regions. For example, the term "antibodies" as used herein comprehends polyclonal and monoclonal antibodies and biologically active fragments thereof including among other possibilities "univalent" antibodies [Glennie et al., *Nature*. 295: 712 (1982)]; Fab proteins including Fab' and F(ab')2 fragments whether covalently or non-covalently aggregated; light or heavy chains alone, preferably variable heavy and light chain regions (VH and VL regions), and more preferably including the hypervariable regions [otherwise known as the complementarity determining regions (CDRs) of said VH and VL regions]; Fc proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., *PNAS* (USA), 79: 6409 (1982)].

It may be preferred for many immunoassays of this invention that biologically active fragments rather than whole antibodies be used. Fab fragments are particularly preferred fragments in accordance with this invention to avoid non-specific binding.

Antibodies for use in the instant invention can be genetically engineered. [See, for example, Morrison et al., *Clin. Chem.*, 34: 1668 (1988); Morrison and Oi, *Adv. Immunol.*, 44: 65 (1989); Rodwell, *Nature*, 342: 99 (1989); Pluckthun, A., *Nature*, 347: 497 (1990); Winter and Milstein, *Nature*, 349: 293 (1991); Pluckthun, A., *Bio/Technology*, 9: 545 (1991); Wetzel, R., *Protein Eng.*, 4: 371 (1991); Geisow, M. J., *Trends Biotechnol.*, 10: 75 (1992); and Chiswell and McCaffery, *Trends Biotechnol.* 10: 85 (1992).] Further bispecific and other types of antibodies [for example, Lerner and Tramanto, *Trends Biochem. Sci.*, 12: 427 (1987); Shokat and Schultz, *Annu. Rev. Immunol.*, 8: 335 (1990); Schultz, P. G., *Science*. 240: 426 (1988); Benkavic et al., *Science*. 250: 1135 (1990); and Lerner et al., *Science*. 252: 659 (1991); Noland and O'Kennedy, *Biochem. Biophys. Acta.*, 1040: 1 (1990); and Bolhuis et al., *Cell Biochem.*, 47: 306 (1991)] can also be used according to this invention.

Standards

Purified reference preparations can be obtained by established procedures. [See, for example, Blithe et al., "Purification of β-core fragment from pregnancy urine and demonstration that its carbohydrate moieties differ from those of native human chorionic gonadotropin-β," *Endocrinol.*, 122: 173–180 (1988).]

Automated Immunoassay System

The methods of this invention can be readily adapted to automated immunochemistry analyzers. To facilitate automation of the methods of this invention and to reduce the turnaround time, anti-UGP antibodies may be coupled to magnetizable particles.

A preferred automated/immunoassay system is the Ciba Corning ACS:180™ Automated Chemiluminescence System [CCD; Medfield, Mass. (USA)]. The Ciba Corning ACS:180™ Automated Immunoassay System is described in Dudley, B. S., *J. Clin. Immunoassay*. 14(2): 77 (Summer 1991). The system uses chemiluminescent labels as tracers and paramagnetic particles as solid-phase reagents. The ACS:180 system accommodates both competitive binding and sandwich-type assays, wherein each of the steps are automated. The ACS:180 uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester.

Solid Phase

The solid phase used in the assays of this invention may be any surface commonly used in immunoassays. For example, the solid phase may be particulate; it may be the surface of beads, for example, glass or polystyrene beads; or it may be the solid wall surface of any of a variety of containers, for example, centrifuge tubes, columns, microtiter plate wells, filters, membranes and tubing, among other containers.

When particles are used as the solid phase, they will preferably be of a size in the range of from about 0.4 to 200 microns, more usually from about 0.8 to 4.0 microns. Magnetic or magnetizable particles such as, paramagnetic particles (PMP), are a preferred particulate solid phase, and microtiter plate wells are a preferred solid wall surface. Magnetic or magnetizable particles may be particularly preferred when the steps of the methods of this invention are performed in an automated immunoassay system.

Preferred detection/quantitation systems of this invention may be luminescent, and. a luminescent detection/quantitation system in conjunction with a signal amplification system could be used, if necessary. Exemplary luminescent labels, preferably chemiluminescent labels, are detailed below, as are signal amplification systems.

Signal Detection/Quantitation Systems

The complexes formed by the assays of this invention can be detected, or detected and quantitated by any known detection/quantitation systems used in immunoassays. As appropriate, the antibodies of this invention used as tracers may be labeled in any manner directly or indirectly, that results in a signal that is visible or can be rendered visible.

Detectable marker substances include radionuclides, such as $^3$H, $^{125}$I, and $^{131}$I; fluorescers, such as, fluorescein isothiocyanate and other fluorochromes, phycobiliproteins, phycoerythin, rare earth chelates, Texas red, dansyl and rhodamine; colorimetric reagents (chromogens); electron-opaque materials, such as colloidal gold; bioluminescers; chemiluminescers; dyes; enzymes, such as, horseradish peroxidase, alkaline phosphatase, glucose oxidase, glucose-6-phosphate dehydrogenase, acetylcholinesterase, α-, β-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatase and paranitrophenyl phosphate (pNPP).

Preferred detection, or detection and quantitation systems according to this invention produce luminescent signals, bioluminescent (BL) or chemiluminescent (CL). In chemiluminescent (CL) or bioluminescent (BL) assays, the intensity or the total light emission is measured and related to the concentration of the analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, Vargulla and Renilla. Luminol can be used optionally with an enhancer molecule, preferably selected from the group consisting of 4-iodophenol or 4-hydroxycinnamic acid. Acridinium esters are one of the preferred types of CL labels according to this invention. A signal is generated by treatment with an oxidant under basic conditions.

Also preferred luminescent detection systems are those wherein the signal is produced by an enzymatic reaction upon a substrate. CL and BL detection schemes have been developed for assaying alkaline phosphatase (AP), glucose oxidase, glucose 6-phosphate dehydrogenase, horseradish peroxidase (HRP), and xanthine-oxidase labels, among others. AP and HRP are two preferred enzyme labels which can be quantitated by a range of CL and BL reactions. For example, AP can be used with a substrate, such as an adamantyl 1,2-dioxetane aryl phosphate substrate (e.g. AMPPD or CSPD; [Kricka, L. J., "Chemiluminescence and Bioluminescence, Analysis by," at p. 167, *Molecular Biology and Biotechnology: A Comprehensive Desk Reference* (ed. R. A. Meyers) (VCH Publishers; N.Y., N.Y.; 1995)]; preferably a disodium salt of 4-methoxy-4-(3-phosphatephenyl)spiro [1,2-dioxetane-3,2'-adamantane], with or without an enhancer molecule, preferably, 1-(trioctylphosphonium methyl)-4-(tributylphosphonium methyl) benzene diochloride. HRP is preferably used with substrates, such as, 2',3', 6'-trifluorophenyl 3-methoxy-10-methylacridan-9-carboxylate.

CL and BL reactions can also be adapted for analysis of not only enzymes, but other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases, and dehydrogenases, and can be used to measure any component of the coupled reaction (enzyme, substrate, cofactor).

The detectable marker may be directly or indirectly linked to an antibody used in an assay of this invention. Exemplary of an indirect linkage of the detectable label is the use of a binding pair between the antibody and the marker, or the use of well known signal amplification signals, such as, using a biotinylated antibody complexed to UGP and then adding streptavidin conjugated to HRP and then TMB.

Exemplary of binding pairs that can be used to link antibodies of assays of this invention to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/anti-dinitrophenol; vitamin B12/intrinsic factor; cortisone, cortisol/cortisol binding protein; and ligands for specific receptor protein/membrane associated specific receptor proteins. Preferred binding pairs according to this invention are biotin/avidin or streptavidin, more preferably biotin/streptavidin.

Various means for linking labels directly or indirectly to antibodies are known in the art. For example, labels nay be bound either covalently or non-covalently. Exemplary antibody conjugation methods are described in: Avarmeas et al., Scan. J. Immunol., 8 (Suppl. 7): 7 (1978); Bayer et al., Meth. Enzymol., 62: 308 (1979); Chandler et al., J. Immunol. Meth., 53: 187 (1982); Ekeke and Abuknesha, J. Steroid Biochem., 11: 1579 (1979); Engvall and Perlmann, J. Immunol., 109: 129 (1972); Geoghegan et al., Immunol. Comm., 7: 1 (1978); and Wilson and Nakane, Immunofluorescence and Related Techniques, p. 215 [Elsevier/North Holland Biomedical Press; Amsterdam (1978)].

Depending upon the nature of the label, various techniques can be employed for detecting, or detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

The following examples are presented to help in the better understanding of the subject invention and are for purposes of illustration only. The examples are not to be construed as limiting the invention in any manner.

Example 1

Seven Singleton Down Syndrome Cases, One Each of Edwards Syndrome, Triploidy and Twins Discordant for Down Syndrome In this example, urine samples were obtained from 10 pregnant women with aneuploid affected pregnancies. The clinical details of all 10 cases are given in Table 1. Seven of the pregnancies were affected with Down syndrome, and the maternal urine samples were taken at gestational ages of from 19 weeks+2 days to 22 weeks+4 days. One of the pregnancies was affected by Edwards syndrome, and the maternal urine sample was taken at 11 weeks+0 days. One pregnancy was discordant for Down syndrome, and the sample was taken at 13 weeks+3 days. The 10th case was a pregnancy affected by triploidy, and the sample was taken at 13 weeks+5 days.

The urine samples were obtained from the women with affected pregnancies immediately following antenatal diagnosis. In one case a confident antenatal diagnosis was made by ultrasound alone (case No. 5 in Table 1). Although the patient in that case refused antenatal diagnosis (amniocentesis) and termination of the pregnancy, she agreed to provide blood and urine samples for research purposes. A confirmatory karyotype was performed at term. The other nine antenatal diagnoses were made by amniocentesis or CVS.

A control series was obtained from the urine samples which are routinely taken for sugar, protein and bacterial analysis from women attending antenatal clinics at the Leeds General Infirmary [University of Leeds, Leeds, U.K.]. Sixty-serum samples from singleton pregnancies with a gestational age ranging from 8 to 24 completed weeks of pregnancy. The mean maternal age in the controls was 27 (range 17 to 42). Urine samples from cases and controls were stored at −40° C. until they were retrieved together for assay.

Each sample was assessed for β-core-hCG, without knowledge of whether it was from a case or a control, using a modification of a previously published radioimmunoassay method [Lee et al., J. Endocrinol., 130: 481–489 (1991)]. The β-core-hCG specific antisera (S504-Immunogen International, Llandyssul, Dyfed SA44 5JT,UK) was retitrated against β-core-hCG tracer in order to give a desensitized assay range of 6–600 pmol/L.

TABLE 1

Clinical Details in Ten Cases of Aneuploidy

| Disorder (Case No.) | Karyotype | Maternal age (years) | Prenatal Diagnosis Method | Reason* | Gestation of Sample (weeks + days) | Outcome |
|---|---|---|---|---|---|---|
| Down syndrome (1) | 47,XY,+21 | 39 | Amniocentesis | Maternal serum test | 19 + 2 | TOP |
| Down syndrome (2) | 47,XY,+21 | 34 | Amniocentesis | Maternal serum test | 19 + 5 | TOP |
| Down syndrome (3) | 47,XY,+21 | 35 | Amniocentesis | Maternal serum test | 21 + 0 | TOP |
| Down syndrome (4) | 47,XX,+21 | 40 | Amniocentesis | Maternal serum test | 21 + 1 | TOP |
| Down syndrome (5) | 47,XY,+21 | 19 | Not done | — | 21 + 4 | Live birth |
| Down syndrome (6) | 47,XX,+21 | 25 | CVS | Ultrasound | 22 + 3 | TOP |
| Down syndrome (7) | 47,XX,+21 | 32 | CVS | Ultrasound | 22 + 4 | TOP |
| Edwards syndrome | 47,XX,+18 | 39 | CVS | Maternal age | 11 + 0 | TOP |
| Twins (Down/normal) | 47,XX,+21/ 46 XY | 36 | CVS | Maternal age | 13 + 3 | TOP |
| Triploidy | 69,XXX | 22 | CVS | Ultrasound | 13 + 5 | TOP |

*The Down syndrome risk reported from the maternal serum test (hCG, alpha-fetoprotein, and unconjugated oestriol) for cases 1–4 was 1 in 12, 1 in 13, 1 in 60, and 1 in 130, respectively. The ultrasound suspicion in case 6 was because of increased nuchal thickness, and in case 7 it was polyhydramnios (mild), hydrocephalus (mild), and calcification within the abdomen.

This assay has a partial mole per mole cross-reaction with intact hCG (6.9%) and free β-hCG (18%) but negligible cross-reactivity with free α-subunit, luteinizing hormone, thyroid stimulating hormone and follicle stimulating hormone (<0.7%). All samples were diluted at 1/100 and 1/1000 prior to assay. Since there was no uniformity in the volume of urine obtained from each woman or the time of voiding, the creatinine content was measured by the Jaffe method using a Monach 200 centrifugal analyzer and the β-core-hCG concentration was expressed in nmol/mmol creatinine.

To allow for gestational differences in β-core-hCG, levels were also expressed as multiples of the normal median (MOM) level for the appropriate gestation derived from the control series. Because of the small number of controls at any week of gestation, and so that MOMs could be calculated to the exact day of gestation, the observed medians were regressed after weighting for the controls. In every case and control, gestational age was based on ultrasound biparietal diameter or crown-rump length measurement.

FIG. 1 shows the β-core-hCG concentration in all 77 samples according to gestation. Among the controls there was a steady decline in levels over the whole period. Log-linear regression fitted this best and the regression equation was: $\log_{10}$ (β-core-hCG)=2.411–0.01320x where x is the gestational age in days. That is equivalent to a 20% weekly fall in concentration.

Table 2 shows the individual values in each case and selected centiles in the controls expressed in MOMs. All seven singleton Down syndrome cases had levels exceeding 2 MOM with a median value of 6.11 MOM—a highly statistically significant elevation (P<0.0005; Wilcoxon Rank Sum Test). There was wide spread of values in the controls exemplified by the 2-fold range between the 25th and 75th centiles or by the 8-fold 10th to 90th centile range. Nonetheless, only 18% (12/67) of values in the controls overlapped with the cases and just 4% (3/67) of them exceeded the median value in the cases.

TABLE 2

Urinary β-core-hCG: Individual Level for each Case and Selected Centiles for 67 Controls (Case Number in Parentheses)

| Sample | β-core-hCG (MOM) |
| --- | --- |
| Cases | |
| Triploidy | 0.02 |
| Edwards syndrome | 0.08 |
| Twin (Down/normal) | 0.64 |
| Down syndrome (1) | 2.39 |
| Down syndrome (2) | 2.97 |
| Down syndrome (7) | 5.63 |
| Down syndrome (3) | 6.11 |
| Down syndrome (4) | 6.24 |
| Down syndrome (6) | 6.54 |
| Down syndrome (5) | 11.91 |
| Controls | |
| 10th centile | 0.45 |
| 25th centile | 0.70 |
| Median | 1.01 |
| 75th centile | 1.56 |
| 90th centile | 3.45 |

The levels were extremely low in the cases of triploidy and Edwards syndrome (0.02 and 0.08 MOM respectively). By comparison the lowest value in the controls was 0.36 MOM. The fetus with triploidy was severely growth retarded and so it may be considered more appropriate to use the menstrual gestation of 17 weeks 5 days rather than the 13 weeks 5 days ultrasound gestation to calculate the MOM value. When that was done, the level increased but only to 0.05 MOM.

The twin pregnancy with Down syndrome did not have a raised β-core-hCG level. That case was considered separately from the singleton Down syndrome pregnancies. Even if it had been included, its inclusion would not have materially altered the overall result. Taking all 8 together the median value was 5.87 MOM (P<0.002; Wilcoxon Rank Sum Test).

There are two important differences between cases and controls that might have biased our results. Firstly, on average maternal age was 5 years more advanced in the cases so that any correlation between age and β-core-hCG could lead to an increase in levels. In fact there was a tendency for levels to decrease with age although this did not reach statistical significance. For example, the median value for the 18 controls aged under 25 was 1.09 MOM, for 25 aged 25-9 it was 1.02 MOM and for the 24 over 30 it was 0.93 MOM. Secondly, in the abnormal pregnancies the sample was usually obtained after an invasive procedure that could have led to an increase in the catabolism of hCG or to feto-maternal transfusion. That is unlikely to have been a factor in view of the low levels in the cases of Edwards syndrome and triploidy, and the fact that the Down syndrome case (number 5) in which such a procedure was not done had the highest MOM value. Moreover, chorionic villus sampling has not been found to raise maternal serum hCG levels [Knott et al., *Eur. J. Obstet. Gynaecol. Reprod. Biol.*, 27: 277–281 (1988)]. A further difference between samples from cases and controls, namely that the former had been stored frozen for longer than the latter (about 5 months on average compared with 1 month) is not important because the β-core fragment of hCG is very stable [de Medeiros et al., *Obstetrics and Gynaecology*, 1: 53–59 (1991)].

EXAMPLE 2

Urinary Multiple Marker Screening

In this example, β-core-hCG levels were detected and quantitated in urine along with two other markers—tE and free α-subunit of hCG (α-hCG). Maternal urine samples were tested from 36 pregnancies affected by aneuploidy (24 Down syndrome, five Edwards syndrome, three Turners syndrome, one Klinefelter syndrome, one triploidy, one triple-X, one twin discordant for Down syndrome) and from 294 controls (unaffected pregnancies), including three pregnancies with twins.

The marker levels were corrected for creatinine excretion and expressed as multiples of the gestation-specific median (MOM) level from singleton controls. The median value for the singleton Down syndrome cases was respectively 6.02, 0.74 and 1.08 MOM for β-core-hCG, tE and α-hCG. The increases in β-core-hCG and the reduction in tE levels were highly significant (P<0.0001 and 0.005, respectively; Wilcoxon Rank Sum Test), but the increase in free α-hCG was not (P=0.40). On the basis of a mathematical model, the expected detection rate for a 5% false-positive rate was 79.6% for β-core-hCG alone which increased to 82.3% when combined with tE. Aneuploidies other than Down syndrome were characterized by low levels of tE and either low or high β-core-hCG.

Methods

Women with affected pregnancies were asked for a urine sample immediately after confirmation of aneuploidy by amniocentesis or placental biopsy. In one case the patient refused antenatal diagnosis following an abnormal ultrasound scan but agreed to provide a urine sample; Down syndrome was confirmed at term. In four cases, because of abnormal ultrasound findings, a sample was taken prior to the diagnostic procedure. Patients were recruited in the area served by the Yorkshire Regional Cytogenetics Laboratory, [Yorkshire, UK] and from those attending selected antenatal clinics at Queen Charlotte's Maternity Hospital [London, UK]. Samples from 36 abnormal cases were available for analysis in the present study: 24 singleton pregnancies with Down syndrome, 5 with Edwardis syndrome, 3 with Turner syndrome, one Klinefelter syndrome, one triploidy, one triple-X and one with twins discordant for Down syndrome. Gestational age ranged from 11 to 23 completed weeks of pregnancy.

A control series was obtained from the urine samples which are routinely taken for sugar, protein and bacterial analysis from women attending antenatal clinics in the Leeds General Infirmary [Leeds, UK] and at Queen Charlotte's Hospital. We selected 294 samples from pregnancies with a similar gestational age range to the cases. On follow up it was found that three of the control pregnancies were twins, and they were considered separately.

Urine samples from cases and controls were stored at −40° C. until retrieved for assay. Each sample was assayed without knowledge of whether it was from a case or a control. β-core-hCG was measured by a radioimmunoassay method [Lee et al., *J. Endocrinol.*, 130: 481–489 (1991)] modified as described in Example 1; tE was measured by a continuous flow system based on the Kober reaction [Lever et al., *Biochem. Med.*, 8: 188–198 (1973)], sensitized by doubling the sample volume and having the concentration of the calibrators previously used for late pregnancy samples.

Free α-hCG was measured using an in-house desensitized radioimmunoassay with a standard range of 500 μg/L, thus requiring samples to be diluted 1/5 or 1/10. The assay uses a polyclonal sheep antibody raised against free α-hCG isolated from a crude commercial preparation of pregnancy urine hCG by gel exclusion and hydrophobic interaction chromatography. An immunoglobulin preparation from the resultant antisera (S781; Polyclonal Antibodies Ltd, Llandyssul, Dyffed, UK) was extensively absorbed against a solid phase of intact hCG conjugated to activated sepharose. This removed antibodies to epitopes present on free α-hCG exposed when it combines with the β-subunit. The NIH reference preparation CR123 was used to prepare assay standards and to form the tracer, by iodination using the chloramine T method. Cross-reactivity with intact hCG, free β-hCG, β-core-hCG, luteinizing hormone (LH), follicle stimulating hormone (FSH) and thyrotropin (TSH) was assessed at 50% of $B/B_o$. Purified reference preparations were obtained from the National Institutes of Health (Bethesda, Md., USA) for intact hCG (CR123), free β-hCG (CR123) and β-core-hCG [donated by Drs. R. Wehmann and D. Blithe; Blithe et al., *Endocrinol.*, 122: 173–180 (1988)] and WHO International Reference Preparations from the National Institute for Biological Standards and Control (Potters Bar, Hertfordshire, UK) for LH (68/40), FSH (83/575) and TSH (80/558). Molecular weights were calculated from the established primary structures: intact hCG 38 kd; free β-hCG 23 kd; free α-hCG 15 kd [Bellisario et al., *J. Biol. Chem.*, 248: 6796 (1973); β-core-hCG 10 kd [Birken et al., *Endocrinol.*, 123: 572 (1988)]; LH 29 kd; FSH 33 kd and TSH 30 kd (Professor S. Jeffcoate, personal communication). On a molar basis the cross-reactivity was <0.01% with free β-hCG and β-core-hCG but higher with intact hCG (10%), LH (8%), FSH (8%) and TSH (6%), possibly caused by dissociation of the purified preparations which would free the α-subunit common to all the glycoprotein hormones.

Since random urines were obtained and there was no uniformity in the time of voiding, the creatinine concentration was measured and the concentrations of the markers were expressed per mmol creatinine. To allow for gestational differences, levels were also expressed as multiples of the normal median (MOM) level for the appropriate gestation derived from the 291 singleton controls. Because of the small number of controls at any week of gestation, and so that MOMs could be calculated to the exact day of gestation, the observed medians in different gestational bands were regressed after weighting for the number in each band. Gestational age was based on ultrasound biparietal diameter or crown-rump length measurement for all cases and controls.

Standard statistical modeling techniques were used to examine the screening potential of each marker and of different multi-marker combinations [Royston and Thompson, *Stats. Med.*, 11: 257 (1992)]. A multivariate log Gaussian frequency distribution was assumed, provided no significant deviation from fit was found in the Shapiro-Wilks Test. If the fit was poor in the extreme tails of the distribution, truncation limits were used. The marker means were estimated by the observed medians, the standard deviations by the 10–90th centile differences divided by 2.563 and the correlation coefficients by the observed values after excluding outliers exceeding 3 standard deviations from the mean. The expected Down syndrome detection rate was calculated for a given false-positive rate from the log Gaussian model, assuming that the maternal age distribution is that of England and Wales in 1989–92 (Office of Population Censuses & Surveys (1991–1994).

Results

The observed median level of each marker in unaffected singleton pregnancies according to gestational age are shown in Table 3. The regressed medians used to calculate MOMs were $10^{2.871-0.01505 \times GA}$ for β-core-hCG, $10^{-1.271+0.01341 \times GA}$ for tE and $10^{-0.170+0.00184 \times GA}$ for α-hCG, where GA is the gestation in days.

TABLE 3

Median Marker Level in Singleton Unaffected Pregnancies According to Gestational Age

| Gestation (wks) | Pregnancies | β-core-hCG | | tE | | α-hCG | |
| --- | --- | --- | --- | --- | --- | --- | --- |
| | | nmol/l | nmol/mmol creatinine | μmol/l | μmol/mmol creatinine | nmol/l | nmol/mmol creatinine |
| <13 | 49 | 273 | 33.7 | 7.0 | 0.71 | 9.7 | 1.06 |
| 13–14 | 77 | 235 | 23.6 | 11.0 | 1.12 | 12.4 | 1.06 |
| 15–16 | 92 | 207 | 21.1 | 14.0 | 1.56 | 10.7 | 0.97 |
| 17–18 | 26 | 73 | 8.0 | 25.5 | 2.70 | 9.8 | 0.92 |
| ≧19 | 47 | 45 | 5.7 | 25.0 | 2.69 | 11.4 | 1.42 |

Table 4 shows the individual MOM values for each of the 24 singleton Down syndrome pregnancies together with the clinical details; for comparison Table 5 shows selected centiles in the 291 singleton controls. All but three cases had β-core-hCG levels exceeding 2 MOM with a median value of 6.02 MOM—a highly significant elevation (P<0.0001; Wilcoxon Rank Sum Test). There was a wide spread of β-core-hCG values in the singleton controls exemplified by the 3-fold range between the 25th and 75th centiles or by the 7-fold 10th to 90th centile range. Nonetheless, only 5 singleton controls (1.7%) exceeded the median value of the abnormal cases.

TABLE 4

Individual Marker Level (MOM)
in 24 Singleton Down Syndrome Pregnancies

| Gestation (wks) | Maternal age (yrs) | Diagnosis* | β-core-hCG | tE | α-hCG |
|---|---|---|---|---|---|
| 11 | 37 | FH → CVS+ | 1.01 | 0.54 | 1.09 |
| 15 | 21 | US → CVS | 3.30 | 1.83 | 0.98 |
| 15 | 24 | FH → CVS | 3.11 | 0.39 | 0.58 |
| 15 | 38 | US → CVS | 1.44 | 0.75 | 1.31 |
| 15 | 38 | MA → CVS | 9.07 | 2.02 | 23.21 |
| 15 | 42 | US → AMN | 1.71 | 0.81 | 2.10 |
| 18 | 28 | MS → CVS | 8.28 | 1.00 | 1.07 |
| 18 | 36 | US → CVS+ | 2.58 | 0.46 | 1.04 |
| 18 | 37 | MS → AMN | 2.93 | 1.11 | 1.25 |
| 19 | 34 | MS → AMN | 2.76 | 0.92 | 0.68 |
| 19 | 38 | MS → AMN | 12.90 | 0.24 | 1.67 |
| 19 | 39 | MS → AMN | 3.93 | 0.43 | 3.38 |
| 19 | 39 | MS → AMN | 2.21 | 1.16 | 0.58 |
| 19 | 42 | MA → AMN | 12.63 | 0.99 | 0.54 |
| 20 | 28 | MS → CVS | 9.67 | 0.72 | 0.59 |
| 20 | 40 | MS → AMN | 6.65 | 0.60 | 0.89 |
| 21 | 20 | MS → AMN | 15.70 | 1.38 | 0.69 |
| 21 | 20 | US** | 11.79 | 0.56 | 1.12 |
| 21 | 28 | MS → CVS | 7.72 | 0.42 | 0.87 |
| 21 | 35 | MS → AMN | 5.94 | 0.74 | 2.62 |
| 21 | 41 | MS → AMN | 6.10 | 0.74 | 5.87 |
| 22 | 25 | US → CVS | 6.64 | 1.21 | 1.98 |
| 22 | 32 | US → CVS | 5.74 | 0.23 | 2.15 |
| 22 | 41 | US → CVS | 6.56 | 0.46 | 0.92 |

*Reasons for carrying out prenatal diagnosis → method used:
FH = family history or chromosomal abnormality;
US = abnormal ultrasound scan;
MS = positive serum screening;
MA = advanced maternal age;
CVS = chorionic villus sampling;
AMN = amniocentesis.
+Urine sample obtained before the prenatal diagnosis.
**Prenatal diagnosis was offered but the patient refused.

TABLE 5

Selected Centiles of Marker Level (MOM)
in 291 Singleton Unaffected Pregnancies

| Centile | β-core-hCG | tE | α-hCG |
|---|---|---|---|
| 10th | 0.38 | 0.60 | 0.54 |
| 25th | 0.66 | 0.80 | 0.68 |
| 50th | 1.04 | 0.99 | 1.00 |
| 75th | 1.66 | 1.35 | 1.61 |
| 90th | 2.50 | 1.77 | 3.22 |

There was a highly statistically significant reduction in tE among the abnormal cases (P<0.005; Wilcoxon Rank Sum Test). However, tE appears to be a less discriminatory marker than β-core-hCG: the median level of 0.74 MOM was at approximately the 20th centile for the singleton controls. The free α-hCG levels in the cases were not significantly different from the controls (P=0.40; Wilcoxon Rank Sum Test).

The twin pregnancy with Down syndrome did not have a raised β-core-hCG level (0.48 MOM) when compared with the two controls (2.43, 3.78 and 8.76 MOM); indeed it was lower than any of the singleton case. The tE level was not particularly low (1.47 compared with 1.23, 2.04 and 5.10 MOM), but the α-hCG was extremely elevated (10.50 compared with 1.14, 4.10 and 7.01 MOM).

The individual MOM values for each of the 11 cases of aneuploidy other than Down syndrome are shown in Table 6. The β-core-hCG levels were either high or low; only one had a MOM value within the 10–90th centile range for the singleton controls. All cases had a tE level below 1 MOM and the median level (0.44 MOM) was highly significantly reduced (P<0.0001; Wilcoxon Rank Sum Test). There was no consistent increase or decrease in free α-hCG levels. Since growth retardation is a feature of some kinds of aneuploidy, it may be considered more appropriate to use menstrual dates rather than the ultrasound gestation to calculate the MOM value. However, in only one case, the triploidy, did the ultrasound scan reduce gestation by more than one week. Using the dates gestation of 17 weeks, the levels of β-core-hCG, tE and α-hCG were 0.04, 0.16 and 0.12 MOM respectively.

TABLE 6

Individual Marker Level (MOM) in
11 Pregnancies with Aneuploidy other than Down Syndrome

| Karyotype | Gestation (wks) | Maternal age (yrs) | Diagnosis* | β-core-hCG | tE | α-hCG |
|---|---|---|---|---|---|---|
| 47,XY,+18 | 14 | 25 | US → CVS+ | 0.33 | 0.66 | 1.31 |
| 47,XY,+18 | 20 | 30 | US → CVS+ | 0.04 | 0.45 | 0.29 |
| 47,XY,+18 | 22 | 24 | US → AMN | 2.19 | 0.18 | 0.47 |
| 47,XX,+18 | 11 | 40 | MA → CVS | 0.06 | 0.16 | 3.16 |
| 47,XX,+18 | 12 | 40 | US → CVS | 0.48 | 0.78 | 1.07 |
| 45,X | 19 | 23 | US → AMN | 7.67 | 0.77 | 1.76 |
| 45,X | 20 | 31 | US → AMN | 0.33 | 0.26 | 0.15 |
| 45,X/ 46,X + ring | 13 | 42 | MA → CVS | 3.35 | 0.37 | 0.60 |
| 47,XXY | 22 | 33 | MS → AMN | 18.50 | 0.58 | 1.42 |

TABLE 6-continued

Individual Marker Level (MOM) in
11 Pregnancies with Aneuploidy other than Down Syndrome

| Karyotype | Gestation (wks) | Maternal age (yrs) | Diagnosis* | β-core-hCG | tE | α-hCG |
|---|---|---|---|---|---|---|
| 69,XXX | 13 | 23 | US → CVS | 0.02 | 0.39 | 0.14 |
| 47,XXX | 23 | 40 | MS → AMN | 6.08 | 0.44 | 1.50 |

*Reasons for carrying out prenatal diagnosis → method used:
US = abnormal ultrasound scan;
MS = positive serum screening;
MA = advanced maternal age;
CVS = chorionic villus sampling;
AMN = amniocentesis.
+Urine sample obtained before the prenatal diagnosis.

A log Gaussian distribution fitted MOM levels for β-core-hCG, tE and both markers combined, provided that extreme outliers were excluded. However, there was a significant deviation from fit for free α-hCG in the controls (P<0.01). Therefore, only the first two of these markers were entered into the model using truncation limits of 0.15–6.0 MOM for β-core-hCG and 0.40–25 MOM for tE. The estimated standard deviation of $\log_{10}$ MOM was 0.32 and 0.34 for β-core-hCG in Down syndrome and unaffected pregnancies respectively; the corresponding values for tE were 0.21 and 0.18. There was virtually no correlation between the two markers. Table 7 shows that expected detection rate for a given false-positive rate based on these parameters. Of the two markers β-core-hCG is by far the more discriminatory with a detection rate for a 5% false-positive rate of 79.6% compared with only 34.2% for tE. Measuring both markers together leads to a further increase in detection of 1.9–5.5%.

TABLE 7

Expected Detection Rate for a Given False-Positive Rate Using β-core-hCG, tE and Both Together

| False-positive rate (%) | β-core hCG | tE | β-core-hCG and tE |
|---|---|---|---|
| 1 | 51.5 | 16.7 | 57.0 |
| 2 | 67.5 | 22.9 | 69.2 |
| 3 | 72.9 | 27.1 | 75.8 |
| 4 | 76.7 | 31.0 | 79.6 |
| 5 | 79.6 | 34.2 | 82.3 |
| 6 | 81.9 | 37.2 | 84.3 |
| 7 | 83.9 | 40.1 | 86.0 |
| 8 | 85.3 | 42.3 | 87.4 |
| 9 | 86.6 | 44.4 | 88.5 |
| 10 | 87.7 | 46.2 | 89.6 |

There are three ways in which the 24 singleton Down syndrome cases differed from controls in this study: maternal age was 7 years more advanced on average; all but three cases had an amniocentesis or CVS prior to obtaining the urine; and 11 cases were selected for antenatal diagnosis because of a positive maternal serum screening test. However, those factors are unlikely to have led to serious bias.

Firstly, only tE showed any degree of correlation with maternal age in singleton controls, and that correlation was not statistically significant. Secondly, CVS does not lead to an increase in maternal serum hCG levels [Knott et al., *Eur. J. Obstet. Gynecol. Reprod. Biol.*, 27: 277 (1988); Barkai et al., *Prenat. Diagn.*, 14: 793 (1994)], and there is no compelling reason to expect that an invasive diagnostic procedure affects urine levels of hCG metabolites and tE. Finally, the marker levels in the cases with positive maternal serum screening tests did not differ markedly from those in other cases (see Table 4). In 21 cases we had paired maternal serum and urine samples: 17 taken simultaneously, one taken a week apart and three after more than 4 weeks. There was only a weak association between serum free β-hCG and urinary β-core-hCG (R=0.22) or free α-hCG (R=0.12) and between serum $uE_3$ and urinary tE (R=0.27) after logarithmic transformation. Furthermore, it is the policy in Leeds [Institute of Epidemiology and Health Service Research, Research School of Medicine, University of Leeds, Leeds, UK] only to screen women aged over 30. As a consequence the detection rate among those screened is high, and the average serum marker levels in true positive tests will not differ substantially from that in unselected Down syndrome pregnancies.

There was little or no increase in free α-hCG levels among the Down syndrome cases. However, the 95% confidence interval around the median (0.8–1.5 MOM) included the average level in maternal serum (1.40 MOM) in a total of 126 affected pregnancies form published series [Cuckle, H. S. (1994) supra]. Thus, without a larger series of tests, urinary free α-hCG is still a candidate urinary marker.

Random urines rather than 24-hour specimens were used in this example, so it was necessary to correct marker levels for the variable concentration of the samples. The standard approach of dividing each value by the creatinine level was used. This appears to have been effective since among unaffected singleton controls, there was no significant correlation between the corrected values, in MOMs, and the creatinine level (P=0.3). Nonetheless variable concentration may have contributed to the wide scatter of β-core-hCG levels in the controls.

The descriptions of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to best explain the principles of the invention and its practical application to enable thereby others skilled in the art to best utilize the invention in various embodiments and with various modifications as are suited to the particular use contemplated. It is intended that the scope of the invention be defined by the claims appended hereto.

All references cited herein are hereby incorporated by reference.

What we claim is:

1. A method for determining a pregnant woman's risk of carrying a fetus with fetal aneuploidy during the second or third trimester of her pregnancy comprising:
   (a) assaying a urine sample from said pregnant woman for β-core-hCG level, wherein said urine sample is obtained during the second or third trimester of her pregnancy;
   (b) comparing the level of β-core-hCG in said urine sample to reference levels of β-core-hCG in urine samples from pregnant women carrying normal fetuses at about the same gestational age as the pregnancy under analysis, said comparison being indicative of said pregnant woman's risk of carrying a fetus with fetal aneuploidy, wherein a higher or lower level of β-core-hCG in the pregnant woman's urine sample than the reference levels is indicative of a risk of the pregnant woman carrying a fetus with fetal aneuploidy.

2. The method according to claim 1 wherein the pregnant woman is in the second trimester of her pregnancy.

3. The method according to claim 1 wherein the urine sample is assayed for β-core-hCG level by immunoassay.

4. The method according to claim 1 wherein the fetal aneuploidy is selected from the group consisting of Down syndrome, Edwards syndrome, triploidy, Turner syndrome, Klinefelter syndrome, and triple-X.

5. The method according to claim 4 wherein the level of β-core-hCG in said urine sample is higher than the reference levels, and the fetal aneuploidy is selected from the group consisting of Down syndrome, Turner syndrome, Klinefelter syndrome and triple-X.

6. The method according to claim 4 wherein the level of β-core-hCG in said urine sample is lower than the reference levels, and the fetal aneuploidy is selected from the group consisting of triploidy and Edwards syndrome.

7. The method according to claim 3 wherein said immunoassay is in a sandwich format or in a competitive assay format.

8. The method according to claim 7 wherein said immunoassay is automated.

9. The method according to claim 3 wherein the level of β-core-hCG in said sample is higher than the reference levels, and said fetal aneuploidy is selected from the group consisting of Down syndrome, Turner syndrome, Klinefelter syndrome and triple-X.

10. The method according to claim 9 wherein said fetal aneuploidy is Down syndrome.

11. The method according to claim 3 wherein the pregnant woman is in the second trimester of her pregnancy.

12. The method according to claim 10 wherein the pregnant woman is in the second trimester of her pregnancy.

13. The method according to claim 4 wherein the pregnant woman is in the second trimester of her pregnancy.

14. The method according to claim 1 further comprising assaying said urine sample for a second marker;
   wherein the level of said second marker in said sample is compared to reference levels of said second marker in urine samples from pregnant women carrying normal fetuses whose pregnancies are at about the same gestational age as the pregnancy under analysis; and
   wherein said comparison is also indicative of said pregnant woman's risk of carrying a fetus with fetal aneuploidy, wherein a higher or lower level of said second marker in said sample than the reference levels for said marker is indicative of a risk of fetal aneuploidy.

15. The method according to claim 14 wherein said second marker is selected from the group consisting of total estrogen (tE), alpha-hydroxydehydroepiandrosterone sulphate (16α-OH-DHAS), pregnancy-associated plasma protein A (PAPP-A), dimeric inhibin, unconjugated estriol (uE$_3$), alpha-fetoprotein (AFP), total estriol (tE$_3$) and proform of eosinophilic major basic protein proMBP).

16. The method according to claim 15 wherein said second marker is selected from the group consisting of PAPP-A, 16 α-OH-DHAS, dimeric inhibin and tE.

17. The method according to claim 1 further comprising determining the pregnant woman's age and average age of women carrying normal fetuses, and comparing the age of the pregnant woman to said average age, wherein if the pregnant woman's age is older than said average age, there is a risk of the pregnant woman carrying a fetus with fetal aneuploidy.

18. The method according to claim 1 further comprising assaying a serum sample from said Dregnant woman for a marker level, comparing the level of said marker in said serum sample to reference levels of said marker in serum samples from pregnant women carrying normal fetuses whose pregnancies are at about the same gestational age as the pregnancy under analysis, said comparison being further indicative of said pregnant woman's risk of carrying a fetus with fetal aneuploidy, wherein a higher or lower level of said marker in said serum sample than said reference levels for said marker is indicative of a risk of the pregnant woman carrying a fetus with fetal aneuploidy.

19. The method according to claim 18 wherein said serum marker is selected from the group consisting of: pregnancy-associated plasma protein A (PAPP-A), major basic protein, proform of eosinophilic major basic protein (proMBP), intact hCG, free α-hCG, free β-hCG, alpha-fetoprotein (AFP), unconlugated estriol (uE$_3$, 16α-hydroxydehydroepiandrosterone sulphate (16α-OH-DHAS.L, dimeric inhibin and nondimeric inhibin.

20. The method according to claim 1 further comprising performing ultrasonography to visualize the fetus carried by said pregnant woman, wherein an abnormal ultrasonograph is indicative of a risk of fetal aneuploidy.

21. The method according to claim 1 wherein the β-core-hCG levels are corrected for variability in urine concentrations by assaying the urine sample for creatinine levels and dividing the β-core-hCG level of each urine sample by the creatinine level for that sample.

22. The method according to claim 1 wherein said β-core-hCG level is determined by methods selected from the group consisting of: chromatography, nuclear magnetic resonance (NMR), fluorometric detection, assaying using non-antibody receptors specific for β-core-hCG, and assaying using binding proteins specific for β-core-hCG.

23. The method according to claim 3 wherein said immunoassay comprises using antibodies which bind specifically to β-core-hCG, and which are directly or indirectly linked to a detectable marker.

24. The method according to claim 23 wherein said immunoassay further comprises using antibodies which bind specifically to β-core-hCG, and which are linked to a solid phase.

25. The method according to claim 23 wherein said detectable marker is selected from the group consisting of radionuclides, fluorescers, bioluminescers, chemiluminescers, dyes, enzymes, coenzymes, enzyme substrates, enzyme cofactors, enzyme inhibitors, enzyme subunits, metal ions, and free radicals.

26. The method according to claim 25 wherein the detectable marker is either selected from the group consisting of acridinium esters, acridinium sulfonyl carboxamides, fluorescein, luminol, umbelliferone, isoluminol derivatives, photoproteins, and luciferases, or is produced by an enzymatic reaction upon a substrate.

27. The method according to claim 23 wherein the detectable marker is either an acridinium ester or is produced by an enzymatic reaction with a chemiluminescent substrate and an enzyme selected from the group consisting of alkaline phosphatase, glucose oxidase, glucose 6-phosphate dehydrogenase, $\alpha,\beta$-galactosidase, horseradish peroxidase, and xanthine oxidase.

28. The method according to claim 24 wherein said solid phase comprises magnetic or paramagnetic particles.

29. The method according to claim 28 wherein said immunoassay is automated, and wherein said detectable marker is an acridinium ester.

* * * * *